US00PP23775P3

(12) United States Plant Patent
Meilland

(10) Patent No.: US PP23,775 P3
(45) Date of Patent: Jul. 30, 2013

(54) HYBRID TEA ROSE PLANT NAMED 'MEISTILEY'

(50) Latin Name: *Rosa hybrida*
Varietal Denomination: Meistiley

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 59 days.

(21) Appl. No.: 13/373,618

(22) Filed: Nov. 22, 2011

(65) Prior Publication Data

US 2013/0111638 P1 May 2, 2013

(30) Foreign Application Priority Data

Oct. 31, 2011 (QZ) ..... PBR 20112569

(51) Int. Cl.
*A01H 5/00* (2006.01)

(52) U.S. Cl.
USPC ..... Plt./140; Plt./130

(58) Field of Classification Search
USPC ..... Plt./130, 140
See application file for complete search history.

*Primary Examiner* — Susan McCormick Ewoldt
(74) *Attorney, Agent, or Firm* — Buchanan Ingersoll & Rooney PC

(57) ABSTRACT

A new and distinct Hybrid Tea rose plant is provided that forms at mid-season abundantly and substantially continuously attractive large very double red blossoms wherein the petals of fully opened blossoms commonly are present in a substantially quartered configuration. The large buds are substantially conical to ovoid in shape. The vegetation is strong and attractive dense leathery glossy dark green foliage is formed. The plant is particularly well suited for the production of cut flowers under greenhouse growing conditions.

1 Drawing Sheet

Figures 1, 2, 3, 4, 5, 6, 7, 8, 9, 10, 11, 12, 13, 14, 15, 16:
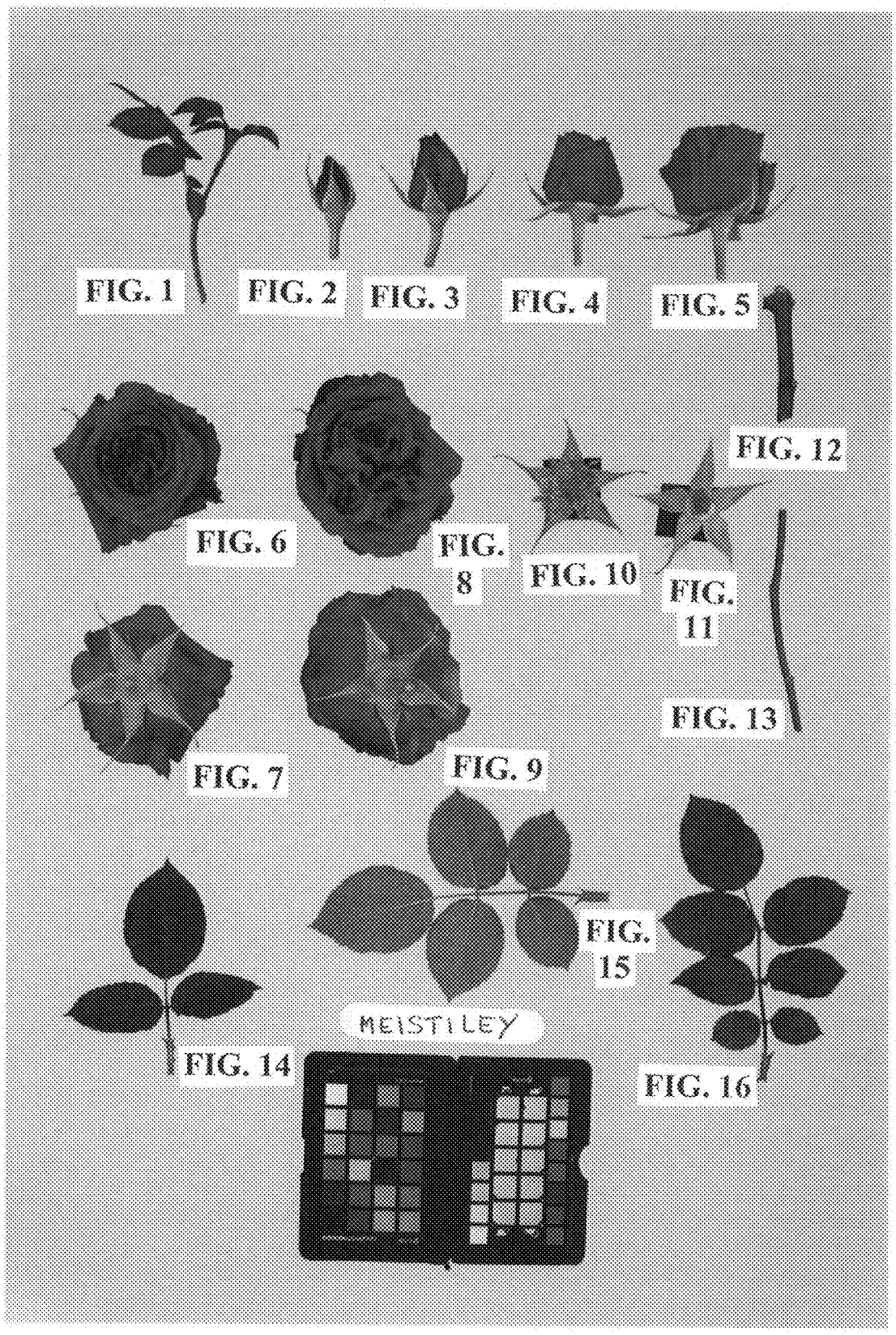

Botanical/commercial classification: *Rosa hybrida*/Hybrid Tea Rose Plant.

Varietal denomination: cv. Meistiley.

SUMMARY OF THE INVENTION

The new variety of *Rosa hybrida* Hybrid Tea rose plant was created by artificial pollination wherein two parents were crossed which previously had been studied in the hope that they would contribute the desired characteristics. The female parent (i.e., the seed parent) was the product of the cross of the 'Meifota' variety (U.S. Plant Pat. No. 5,683) and the 'Veramal' variety (non-patented in the United States). The male parent (i.e., the pollen parent) was the product of the cross of the 'Meibuito' variety (non-patented in the United States) and the 'Meibigoud' variety (U.S. Plant Pat. No. 9,308).

The parentage of the new variety can be summarized as follows:

('Meifota'×'Veramal')×('Meibuito'×'Meibigoud').

The seeds resulting from the above pollination were sown and small plants were obtained which were physically and biologically different from each other. Selective study resulted in the identification of a single plant of the new variety.

It was found that the new Hybrid Tea rose plant of the present invention:

(a) displays an erect growth habit with strong vegetation,
(b) forms large substantially conical- to ovoid-shaped buds,
(c) forms at mid-season abundantly and substantially continuously large very double red blossoms wherein the petals commonly display a long vase life and wherein the petals of fully opened blossoms commonly are present in a substantially quartered configuration, (d) displays attractive dense leathery glossy dark green foliage, and
(e) is particularly well suited for the production of cut flowers under greenhouse growing conditions.

The new variety well meets the needs of the horticultural industry and can be grown to advantage during the commercial production of cut flowers.

The new variety can be readily distinguished from its ancestors. For instance, the blossom appearance is considerably different from that of the 'Meifota', 'Veramal' and 'Meibuito' varieties. More specifically, the 'Meifota' variety forms dark salmon pink blossoms, the 'Veramal' variety forms orange-red blossoms, and the 'Meibuito' variety forms darker red blossoms. The 'Meibigoud' variety forms considerably longer stems than the new variety.

Additionally, the new variety can be readily distinguished from other Hybrid Tea cut-flower rose varieties, such as 'Meivanthou' (U.S. Plant Pat. No. 16,493) and 'Meikatana' (U.S. Plant Pat. No. 19,471). For instance, the 'Meivanthou' variety forms a substantially lesser number of stems and forms blossoms which do not open as fully as those of the new variety. The 'Meikatana' variety forms blossoms having a greater depth and a more lanceolate leaflet configuration than the new variety.

The new variety has been found to undergo asexual propagation in France by a number of routes, including budding, grafting, and the use of cuttings. Asexual propagation by the above-mentioned techniques at Le Cannet des Maures, Var, France, has shown that the characteristics of the new variety are stable and are strictly transmissible by such asexual propagation from one generation to another. Accordingly, the new variety undergoes asexual propagation in a true-to-type manner.

The new variety has been named 'Meistiley'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during April while growing on their own roots outdoors at Le Cannet des Maures, Var, France. A standard color presentation is included at the bottom of the photograph for comparative purposes.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a main branch;

FIG. 13—illustrates a specimen of a flowering stem;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

The chart used in the identification of the colors is that of The Royal Horticultural Society (R.H.S. Colour Chart). The description is based on the observation of one-year-old plants during June while growing on their own roots outdoors at Le Cannet des Maures, Var, France.

Class: Hybrid Tea.

Plant:

*Growth habit.*—Erect.

Branches:

*Color.*—Young stems: near Yellow-Green Group 146A. Adult wood: near Yellow-Green Group 147B.

*Stem number.*—Typically approximately 6.5 stems per plant on average. This compares to approximately 3.5 stems per plant for the 'Meivanthou' variety.

*Stem length.*—Typically approximately 75.4 cm on average.

*Stem diameter.*—Typically approximately 7.3 mm on average.

*Thorns.*—None observed.

Leaves:

*Stipules.*—Adnate, pectinate, rather broad, approximately 2 cm in length on average, approximately 0.4 cm in width on average, near Green Group 138B on the upper surface, and near Yellow-Green Group 146C on the under surface.

*Petioles.*—Upper surface: near Green Group 138B in coloration. Under surface: near Yellow-Green Group 146C in coloration. Length: approximately 5.5 cm on average for the terminal leaflet. Texture: glandular on the upper surface, and lacking prickles on the under surface.

*Rachis.*—Upper surface: near Yellow-Green Group 147B in coloration. Under surface: near Yellow-Green Group 146C in coloration. Texture: smooth.

*Size.*—Length: typically approximately 18.4 cm on average for a five-leaflet leaf. Width: typically approximately 15 cm on average for a five-leaflet leaf.

*Leaflets.*—Number 3, 5 (most often), and 7. Shape: generally oval with a cuspidate tip and an obtuse base. General appearance: dense with a glossy aspect. Serration: small and single (as illustrated). Texture: physically firm and leathery. Color (young foliage): Upper surface: near Green Group 139A. Under surface: near Green Group 137C. Color (adult foliage): Upper surface: near Green Group 137A. Under surface: near Green Group 138B.

*Venation.*—Typical rose pattern as illustrated and commonly of substantially the same coloration as the leaflets on both surfaces.

Inflorescence:

*Number of flowers.*—Commonly approximately 1 blossom per stem. On Apr. 13, 2013 when near six stems per plant were observed there were near 6 blooms per plant.

*Peduncle.*—Smooth, approximately 7.5 cm in length on average, approximately 0.7 cm in diameter on average, and near Yellow-Green Group 144A in coloration.

*Sepals.*—Upper surface: tomentose and near Yellow-Green Group 147C and 147D in coloration. Under surface: smooth and near Yellow-Green Group 144A in coloration. Shape: longish-pointed and narrow, and rounded at the base. Size: approximately 3.5 cm in length on average, and approximately 1.3 cm in width at the widest point on average.

*Buds.*—Shape: substantially conical to ovoid. Size: large. Length: approximately 2.5 cm on average. Width: approximately 2 cm at the widest point on average. Color as calyx breaks: Upper surface: near Red Group 53A suffused with near Red-Purple Group 59A. Under surface: near Red Group 53A.

*Flower.*—Shape: cup-shaped. Diameter: approximately 10 cm on average. Height: approximately 4.5 cm on average. This compares to a greater height of approximately 6 cm for the 'Meikatana' variety. Color (in the course of opening): Upper surface: near Red Group 46A suffused with near Red Group 53A. Under surface: near Red Group 53B. Color (open flower): Upper side: near Red Group 53B. Under side: near Red Group 53D. Fragrance: none. Petal number: commonly approximately 75 to 77 on average under normal growing conditions. Petal shape: with a substantially rounded tip and a substantially rounded base. Petal texture: leathery and somewhat firm. Petal length: approximately 4.5 to 5.5 cm on average. Petal width: approximately 4 to 6 cm on average. Petal arrangement: imbricated, and without petaloids. Vase life: long, and commonly approximately 12 to 14 days on average. Petal drop: good with the petals commonly detaching cleanly before drying. Stamen number: approximately 92 on average. Anthers: regularly arranged in a whorl around the styles, approximately 0.2 cm in size on average, and near Orange Group 26B in coloration. Filaments: approximately 0.5 to 0.8 cm in length on average, and near Orange-Red Group 34A in coloration. Pistils: approximately 153 on average. Stigmas: approximately 0.2 cm in size on average, and near Yellow Group 11D in coloration. Styles: approximately 0.8 to 1 cm in length on average, and near Orange-Red Group 34A in coloration. Receptacle: smooth, funnel-shaped in longitudinal section, approximately 1 cm in length on average, approximately 1.5 cm in width on average at the widest point, and near Yellow-Green Group 146C in coloration.

Development:

*Vegetation.*—Strong.

*Blooming.*—Mid-season, very abundant and substantially continuous.

*Tolerance to diseases.*—Good, with no particular susceptibility to common diseases having been encountered during observations to date.

I claim:

1. A new and distinct Hybrid Tea rose plant characterized by the following characteristics:

(a) displays an erect growth habit with strong vegetation, (b) forms large substantially conical- to ovoid-shaped buds, (c) forms at mid-season abundantly and substantially continuously large very double red blossoms wherein the petals commonly display a long vase life and wherein the petals of fully opened blossoms commonly are present in a substantially quartered configuration, (d) displays attractive dense leathery glossy dark green foliage, and (e) is particularly well suited for the production of cut flowers under greenhouse growing conditions;

substantially as shown and described.

* * * * *

MEISTILEY